(12) United States Patent
Claassen

(10) Patent No.: US 6,232,451 B1
(45) Date of Patent: May 15, 2001

(54) PROCESS FOR THE PREPARATION OF ORGANIC AZIDES

(75) Inventor: Henricus Cornelis Jozephus Claassen, Rijkevoort (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/499,685

(22) Filed: Feb. 8, 2000

(30) Foreign Application Priority Data

Feb. 19, 1999 (EP) .................................................. 99200484

(51) Int. Cl.[7] .......................... C07H 5/04; C07C 247/06; C07C 247/16; C07B 43/00
(52) U.S. Cl. .............................. 536/18.7; 536/124; 552/1; 552/10
(58) Field of Search .................................. 536/18.7, 124; 552/1, 10

(56) References Cited

U.S. PATENT DOCUMENTS

| 3,893,997 | 7/1975 | Cooper et al. ........................ 260/210 |
| 4,582,918 | * 4/1986 | Nagabhushan et al. .............. 549/525 |
| 5,731,464 | * 3/1998 | Ogasawara ........................... 564/428 |

OTHER PUBLICATIONS

Saito, S. et al "Selective C-2 opening of 2,3-epoxyesters with HN3-amine system" Tet. Lett., vol. 32, No. 5, pp. 667–670, 1991.*

Ghosh, A. K., et al "A convenient enzymatic route to optically active 1-aminoindan-2-ol" Synthesis, vol. 5, pp. 541–544, 1997.*

Capek, K. et al "Preparation of methyl 2,4-diacetamido-2, 4,6-trideoxy-alpha-D-ido- . . . alpha-D-mannopyranoside" vol. 52, pp. 2248–2259, 1986.*

Zamojski, A. et al.: "The synthesis of derivatives of 2,4-diamino-2,4,4-trideoxy-D-gulo- and L-altro-hexopyranoses" Carbohydr. Res. vol. 279, 1995.

Thomson, R. and V. Itzstein, M.: "Synthesis of 4-substituted-2-acetamido-2,4-dideoxymannopyranoses using 1,6-anhydro sugar chemistry" Carbohydr. Res. vol. 274, 1995.

Gnichtel, H. and Rebentisch, D.: "Synthesis of amino sugars from tri-O-acetyl-D-glucal via epoxides" J. Org. Chem. vol. 47, 1982.

* cited by examiner

*Primary Examiner*—Howard C. Lee
*Assistant Examiner*—Leigh C. Maier
(74) *Attorney, Agent, or Firm*—William M. Blackstone

(57) ABSTRACT

A process for the addition of an azide function to an organic compound in which process a mixture is prepared by adding an epoxide-derivative of the organic compound and an alkali metal azide salt to a solvent is described. The mixture is heated to a reaction temperature at which the epoxide-derivative and the azide can react to form an azide derivative of the organic compound. An amount, near equimolar to the epoxide derivative, of a (1–6C)alkyl-(2–4C)carboxylic acid ester having a boiling point above the reaction temperature is added to the mixture before and/or during the reaction.

7 Claims, 2 Drawing Sheets

PROCESS FOR THE PREPARATION OF ORGANIC AZIDES

FIELD OF INVENTION

Figure 1:
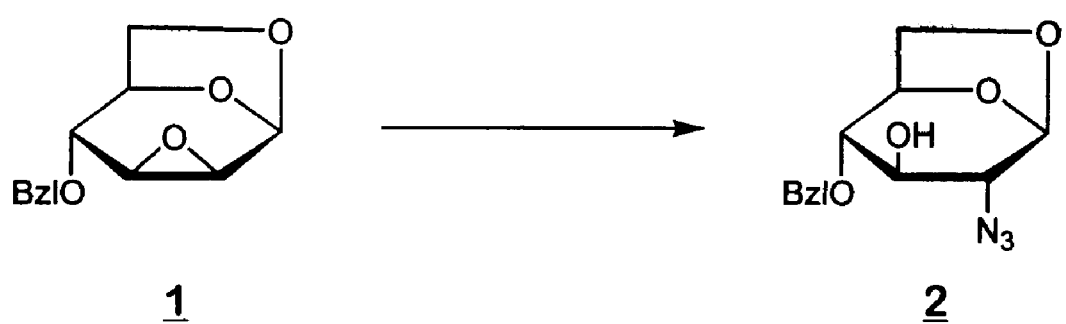

The invention relates to a process for the addition of an azide function to an organic compound. In such a process an epoxide-derivative of the organic compound and an alkali metal azide salt react in a solvent to form an azide derivative of the organic compound.

BACKGROUND OF INVENTION

An azide function is often introduced in an organic molecule, in particular in a carbohydrate, during a multistep synthesis of compounds with amino groups. The introduction of the azide function can be accomplished by either azide substitution of an appropriate leaving group, such as tosylate, mesylate or chloride, or by addition of the azide-anion to an epoxide. For example, azidohydrins, potential precursors for 1,2-aminoalcohols can be prepared from epoxides by reaction with an alkali metal azide under alkaline or acidic conditions.

In most processes known in the art for the azide addition to an epoxide the process is carried out in a polar organic solvent at a temperature of approximately 100–110° C., in combination with a buffering system such as ammoniumchloride, ammoniumsulphate, or tri-isopropylbenzenesulfonic acid/2,6-lutidine (Van Boeckel, et al., J. Carbohydr. Chem. 1985, 4, 293–321). Problems encountered with such processes is that side reactions may occur by the acidic or alkaline conditions leading to isomerisation, epimerisation, and rearrangement. A further serious drawback of the use of an ammonium salt is that ammoniumazide is formed, which is considered to be an explosive compound, and upon using ammoniumchloride also chloride can add to the epoxide instead of azide. The use of buffers consisting of a mixture of an organic base and an acid for pH control may give rise to the formation of hydrazoic acid. This is a highly toxic and explosive gas. In general, reactions with alkali metal azides cannot be performed in a stainless steel reactor, because there is a possibility that heavy metal azides, such as chromium- or nickel azide, are formed upon contact with the walls of the reactor. Such heavy metal azides are explosive in dry form. Furthermore the azide ion has the same corrosive properties as for instance the chloride or bromide ion. On the other hand, in a glass lined reactor serious corrosion of the glass lining at temperatures of 100–110° C. also occurs. In particular this occurs under basic conditions when, for example, in using sodiumazide in water and dimethylformamide, the pH can rise to values over 12 due to the formation of sodiumhydroxide.

SUMMARY OF THE INVENTION

It is found now that one or more of the mentioned disadvantages of known processes for the addition of an azide function to an organic compound can be avoided if an amount, near equimolar to the epoxide derivative, of a (1–6C)alkyl-(2–4C)carboxylic acid ester having a boiling point above the reaction temperature is added to the reaction mixture before and/or during the reaction.

DETAILED DESCRIPTION OF THE INVENTION

The term (1–6C)alkyl refers to a straight or branched alkyl group having 1–6 carbon atoms and (2–4C)carboxylic acid refers to a straight or branched carboxylic acid having 2–4 carbon atoms.

The presence of such an ester in the reaction mixture provides for maintenance of the pH within a reasonable range during formation of the organic azide. The ester is saponified by the hydroxide ions generated during the reaction and in this way the pH is kept below 10. Using this procedure the azide addition reaction can be performed safely in a glass lined reactor without formation of hydrazoic acid and without corrosion of the glass layer of the reactor wall.

Esters can be used which have a boiling point above the reaction temperature. The boiling point should be above this temperature otherwise the ester would boil out of the reaction mixture. Examples of suitable esters are (1–6C)alkylformates, (1–5C)alkylacetates, (1–4C)alkylpropionates, (1–3C)alkylbutyrate, while butylacetate is a preferred ester.

The reaction mixture is heated to a reaction temperature at which the epoxide-derivative and the azide can react to form an azide derivative of the organic compound. Usually, the reaction temperature is between 60 and 120° C. Preferably, the reaction temperature is maintained until the reaction is completed.

The molar ratio between the added amount of ester and the added amount of the epoxide during the reaction should be near equimolar to the epoxide derivative. Usually near equimolar is a ratio within the range of from 0.9 to 1.1. A ratio of 1.0 is preferred. A ratio of less than 0.9 might eventually allow the pH to reach a value over 12 with negative consequences for the glass lining of the reactor and a ratio of more than 1.1 might lead to the formation of alkanoic acid with which alkali metal azide can generate the volatile, toxic and explosive hydrazoic acid.

The ester can be added to the reaction mixture before the start of the reaction or during the reaction or both before and during the reaction, although for practical reasons it is preferred to add the ester before the start of the reaction.

The process of this invention can be used for the preparation of an azide derivative adjacent to a hydroxyl function of any organic compound capable of carrying an epoxide function. Examples of organic compounds carrying an epoxide function for the process are stryrene oxide, 2,3-epoxybutane, indene oxide, but preferred organic compounds are carbohydrate derivatives with an epoxide function. The use in the process of epoxy derivatives of 1,6:2,3-dianhydro-4-O-phenylmethyl-β-D-mannopyranose or 1,6:2,3-dianhydro-4-O-[2,3-bis-O-phenylmethyl-4,6-O-phenylmethylidene-β-D-glucopyranosyl]-β-D-mannopyranose or 1,6:2,3-dianhydro-4-O-[2,3-bis-O-phenylmethyl4,6-O-( 1-methylethylidene)-β-D-glucopyranosyl]-β-D-mannopyranose are more preferred. The further preferred use of the process is for the formation of 2-azido-2-deoxy-pyranose, which is a precursor for a glycosamine moiety in a glycosaminoglycan with antithrombotic properties.

Alkali metal azides which can be used are lithium azide, potassium azide and sodium azide, whereby sodium azide is preferred.

Many different types of solvent can be used in the process, for example ethanol, acetonitril, dimethylsulfoxide or hexamethylene. Preferred is the use of a polar aprotic solvent, which is a solvent which is miscible with water, has a high dielectric constant ($\in > 15$) and is incapable of donating hydrogen for formation of hydrogen bridges. Preferred solvents are dimethylformamide, N-methylpyrrolidinone or dimethylacetamide. N-methylpyrrolidinone is most preferred when carbohydrates are azidised. Preferably, water is added to the solvent in order to allow for a higher concentration of the water soluble alkali metal azide salt in the reaction mixture. A considerable amount of water, up to an equal volume to the organic solvent, can be present in the reaction mixture.

The addition reaction can usually take place at reaction temperatures ranging from 60–120° C. and preferably at 110° C.

The completion of the addition reaction can be determined by measurement of components in the mixture with methods generally known to the skilled person. The reaction can last from one hour to several days depending upon the reactivity of the organic epoxide and on the various compounds in the mixture. When no substantial increase in the amount of organic azide, formed during the reaction, is observed or the amount of products from unwanted side reactions increases, the reaction is completed.

The following example is described for illustration of the invention.

LEGENDS TO THE FIGURES

FIG. 1: Reaction scheme for synthesis of 1,6-anhydro-2-azido-4-O-phenylmethyl-2-deoxy-β-D-glucopyranose.

Figure 2:
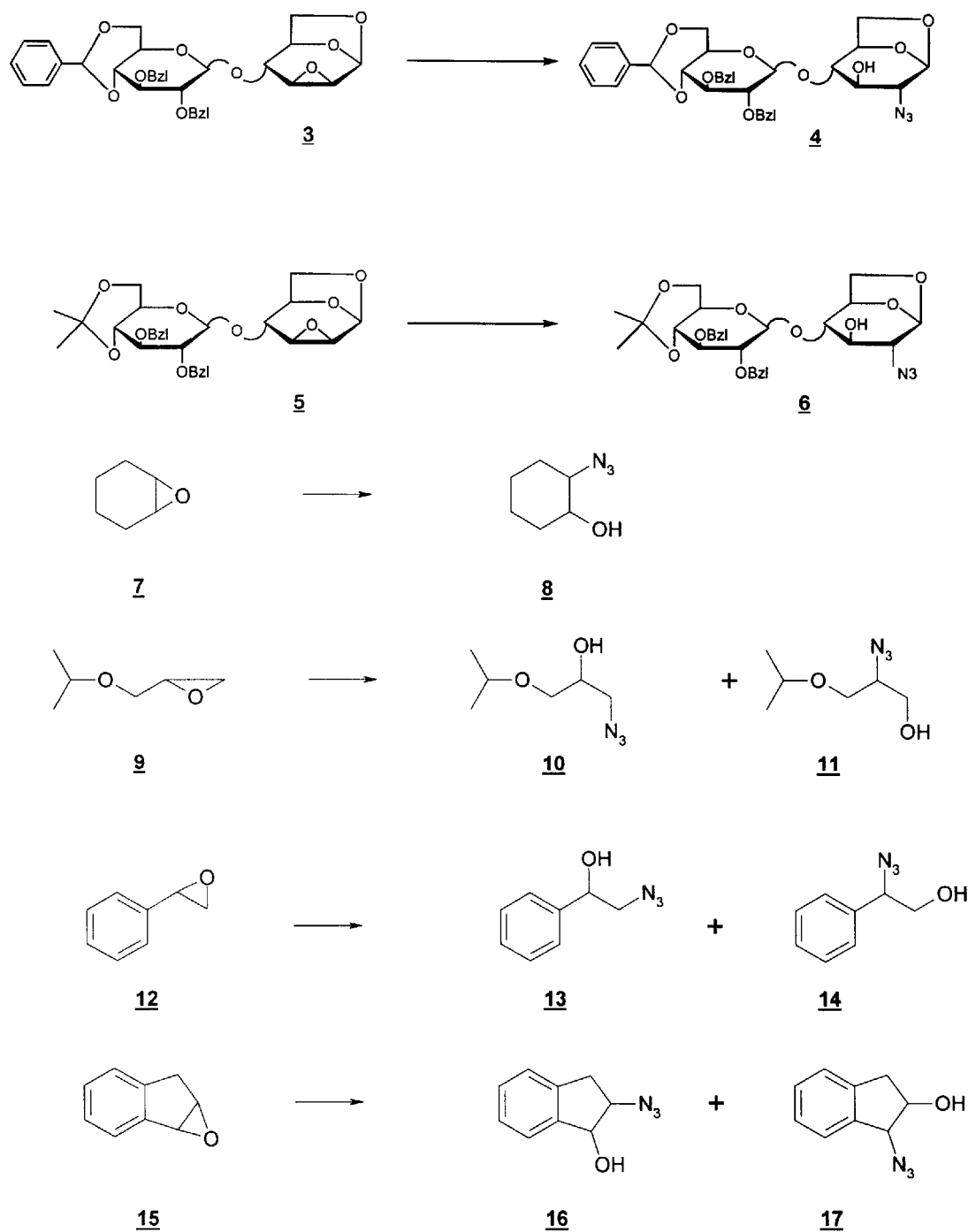

FIG. 2: Reaction schemes for addition of azide functions to the following epoxides: 1,6:2,3-dianhydro-4-O-[2,3-bis-O-phenylmethyl-4,6-O-phenylmethyl-idene-β-D-glucopyranosyl]-β-D-mannopyranose, 1,6:2,3-dianhydro4-O-[2,3-bis-O-phenylmethyl-4,6-O-(1-methylethylidene)-β-D-glucopyranosyl]-β-D-mannopyranose, cyclohexene oxide, glycidyl isopropyl ether, styrene oxide, and indene oxide.

EXAMPLE

Protocol for the azide addition on 1,6:2,3-dianhydro-4-O-phenylmethyl-β-D-mannopyranose.

10.88 kg 1,6:2,3-dianhydro-4-O-phenylmethyl-β-D-mannopyranose (1 in FIG. 1) was dissolved in 54.4 L 1-methyl-2-pyrrolidone in a glass lined reactor. 6113 ml n-butylacetate, 9028 g sodium azide and 38 L water were added. The mixture was warmed at 100°–110° C. and stirred for 20 hrs at 100°–110° C. The mixture was cooled at 25° C. and water and ethylacetate were added. The product was isolated from the reaction mixture by extraction with ethylacetate.

The ethylacetate extract is evaporated at 60° C. in vacuum while introducing water and the product is crystallised from water at 30° C. After filtration, washing and drying the yield was 11.935 kg 1,6-anhydro-2-azido-4-O-phenylmethyl-2-deoxy-β-D-glucopyranose (2 in FIG. 1). TLC: toluene/ethylacetate 70/30 $R_F$: 0.35; melting point: 98.4° C. Further identification: $^1$H NMR in CDCl$_3$ and chemical shifts relative to TMS set at 0 parts per million:

| Position | δ | Multiplicity |
|---|---|---|
| H1 | 5.47 | S |
| H2 | 3.23 | D |
| H3 | 3.88–3.92 | Ddd |
| H4 | 3.38 | M |
| H5 | 4.62 | Dd |
| H6 | 3.70 | Dd |
| H6' | 3.94 | Dd |
| CH$_2$ from benzyl | 4.70 | D |
| Aromatic protons | 7.29–7.40 | M |
| OH | 2.43 | D |

This reaction was performed on the following epoxides according to the method described above:

1,6:2,3-dianhydro-4-O-[2,3-bis-O-phenylmethyl-4,6-O-phenylmethylidene-β-D-glucopyranosyl]-β-D-mannopyranose (3 in FIG. 2) yielding 1,6-anhydro-2-azido-4-O-[2,3-bis-O-phenylmethyl-4,6-O-phenylmethylidene-β-D-glucopyranosyl]-2-deoxy-β-D-glucopyranose (4 in FIG. 2). TLC: toluene/ethylacetate 70/30 on silica, $R_F$: 0.42.

1,6:2,3-dianhydro-4-O-[2,3-bis-O-phenylmethyl4,6-O-(1-methylethylidene)-β-D-glucopyranosyl]-β-D-mannopyranose (5 in FIG. 2) yielding 1,6-anhydro-2-azido-4-O-[2,3-bis-O-phenylmethyl-4,6-O-(1-methylethylidene)-β-D-glucopyranosyl]-2-deoxy-β-D-glucopyranose (6 in FIG. 2). TLC: dichloromethane/acetone 90/10, $R_F$: 0.50.

Cyclohexene oxide (7 in FIG. 2) yielding 2-azidocyclohexanol (8 in FIG. 2). TLC: dichloromethane/methanol 60/40, RF: 0.93.

Glycidyl isopropyl ether (9 in FIG. 2) yielding, according to NMR, a 9:1 mixture of 3-azido-2-hydroxypropyl isopropyl ether (10 in FIG. 2) and 2-azido-3-hydroxypropyl isopropyl ether (11 in FIG. 2). TLC: methanol, RF: 0.75.

Styrene oxide (12 in FIG. 2) yielding, according to NMR, a 1:1 mixture of 2-azido-1-phenyl ethanol (13 in FIG. 2) and 2-azido-2-phenyl ethanol (14 in FIG. 2). TLC: dichloromethane/methanol 60/40, RF: 0.90.

Indene oxide (15 in FIG. 2) yielding, according to NMR, 2-azidoindan-1-ol (16 in FIG. 2) and/or 1-azidoindan-2-ol (17 in FIG. 2). TLC: toluene/ethylacetate 1/1, RF: 0.74.

What is claimed is:

1. A process for the addition of an azide function to an organic compound, comprising reacting in a solvent an epoxide-derivative of the organic compound and an alkali metal azide salt to form an azide derivative of the organic compound, wherein an amount, near equimolar to the epoxide derivative, of a (1–6C)alkyl-(2–4C)carboxylic acid ester having a boiling point above the reaction temperature is added to the reaction mixture before and/or during the reaction.

2. A process according to claim 1, wherein the epoxide-derivative of the organic compound is selected from the group consisting of stryrene oxide, 2,3-epoxybutane, indene oxide, and an epoxy derivative of a carbohydrate.

3. A process according to claim 2, wherein the epoxide-derivative of the organic compound is an epoxy derivative of a carbohydrate.

4. A process according to claim 3, wherein the epoxide-derivative of a carbohydrate is 1,6:2,3-dianhydro-4-O-phenylmethyl-β-D-mannopyranose or 1,6:2,3-dianhydro-4-O-[2,3-bis-O-phenylmethyl-4,6-O-phenylmethylidene-β-D-glucopyranosyl]-β-D-mannopyranose or 1,6:2,3-dianhydro-4-O-[2,3-bis-O-phenylmethyl-4,6-O-(1-methylethylidene)-β-D-glucopyranosyl]-β-D-mannopyranose.

5. A process according to claim 1, wherein the reaction temperature is between 60 and 120° C.

6. A process according to claim 1, wherein the ester is butylacetate.

7. A process according to claim 1, wherein water is added to the reaction mixture in an amount of at most equal to the volume of the solvent.

* * * * *

UNITED STATES PATENT AND TRADEMARK OFFICE
CERTIFICATE OF CORRECTION

PATENT NO. : 6,232,451 B1
DATED : May 15, 2001
INVENTOR(S) : Claassen

It is certified that error appears in the above-identified patent and that said Letters Patent is hereby corrected as shown below:

<u>Title page,</u>
Item [73], should read:
-- Assignee: Akzo Nobel N.V. (NL) and Sanofi-Synthelabo --

Signed and Sealed this

Fifth Day of November, 2002

Attest:

Attesting Officer

JAMES E. ROGAN
*Director of the United States Patent and Trademark Office*